United States Patent
Huo et al.

(10) Patent No.: US 10,401,167 B2
(45) Date of Patent: Sep. 3, 2019

(54) WEARABLE AMBIENT PRESSURE GAUGE

(71) Applicant: Apple Inc., Cupertino, CA (US)

(72) Inventors: Edward S. Huo, San Francisco, CA (US); Scott A. Myers, Saratoga, CA (US); Martin J. Auclair, Cupertino, CA (US); William C. Lukens, San Franciso, CA (US); Tyler S. Bushnell, Mountain View, CA (US)

(73) Assignee: APPLE INC., Cupertino, CA (US)

( * ) Notice: Subject to any disclaimer, the term of this patent is extended or adjusted under 35 U.S.C. 154(b) by 265 days.

(21) Appl. No.: 14/857,540

(22) Filed: Sep. 17, 2015

(65) Prior Publication Data

US 2017/0082433 A1    Mar. 23, 2017

(51) Int. Cl.

| | |
|---|---|
| *G01C 5/06* | (2006.01) |
| *G01L 23/10* | (2006.01) |
| *G01L 1/00* | (2006.01) |
| *G06F 1/16* | (2006.01) |
| *G01L 1/26* | (2006.01) |
| *G04G 21/02* | (2010.01) |
| *G04G 21/08* | (2010.01) |
| *G06F 3/0362* | (2013.01) |
| *A61B 5/00* | (2006.01) |

(52) U.S. Cl.
CPC .............. *G01C 5/06* (2013.01); *A61B 5/681* (2013.01); *A61B 5/6802* (2013.01); *G01L 1/00* (2013.01); *G01L 1/26* (2013.01); *G01L 23/10* (2013.01); *G04G 21/02* (2013.01); *G04G 21/08* (2013.01); *G06F 1/163* (2013.01); *G06F 1/1684* (2013.01); *G06F 3/0362* (2013.01); *A61B 2562/0261* (2013.01)

(58) Field of Classification Search
CPC ........................................................ G01C 5/06
See application file for complete search history.

(56) References Cited

U.S. PATENT DOCUMENTS

| | | | |
|---|---|---|---|
| 4,389,711 A * | 6/1983 | Hotta | G06F 3/0414 |
| | | | 178/18.03 |
| 4,783,772 A | 11/1988 | Umemoto et al. | |
| 4,835,716 A | 5/1989 | Tamaki et al. | |
| 5,737,246 A | 4/1998 | Furukawa et al. | |
| 8,359,172 B2 | 1/2013 | Fattah | |
| 2010/0123686 A1* | 5/2010 | Klinghult | G06F 3/0412 |
| | | | 345/178 |
| 2011/0003665 A1* | 1/2011 | Burton | G04F 10/00 |
| | | | 482/9 |

(Continued)

*Primary Examiner* — Justin Seo
*Assistant Examiner* — John M Royston
(74) *Attorney, Agent, or Firm* — Dorsey & Whitney LLP

(57) ABSTRACT

An electronic device includes at least a housing having a force transmissive surface capable of receiving a force, a force sensor configured to sense the force received from the force transmissive surface in accordance with a force path and respond by outputting a signal that indicates a magnitude of the force at a first sensitivity level when the magnitude of the force is less than a threshold level, otherwise, the signal indicates the magnitude of the force in accordance with a second sensitivity level. The electronic device includes a processor in communication with the force sensor that uses the signal to alter an operation of the electronic device. In one embodiment, the electronic device is wearable.

20 Claims, 10 Drawing Sheets

(56) References Cited

U.S. PATENT DOCUMENTS

| | | | |
|---|---|---|---|
| 2012/0318070 A1* | 12/2012 | Evans | G01L 25/00 |
| | | | 73/862.68 |
| 2012/0323496 A1* | 12/2012 | Burroughs | G06F 19/3481 |
| | | | 702/19 |
| 2014/0085213 A1* | 3/2014 | Huppi | 345/173 |
| 2016/0313839 A1* | 10/2016 | Hou | G06F 3/03545 |

* cited by examiner

WEARABLE AMBIENT PRESSURE GAUGE

FIELD

The following disclosure relates to an electronic device. In particular, the following disclosure relates to a wearable electronic device that can be used to determine and evaluate external environmental factors, such as an external ambient pressure.

BACKGROUND

Electronic devices may include certain features to enhance a user experience. For example, an electronic device may include a sensing element designed to monitor the user. In particular, a wearable electronic device can include multiple force sensors used for interacting with a user as well as provide environmental information.

SUMMARY

In one aspect, an electronic device is described. The electronic device includes at least a housing having a force transmissive surface capable of receiving a force, a force sensor configured to sense the force received from the force transmissive surface in accordance with a force path and respond by outputting a signal that indicates a magnitude of the force at a first sensitivity level when the magnitude of the force is less than a threshold level, otherwise, the signal indicates the magnitude of the force in accordance with a second sensitivity level. The electronic device includes a processor in communication with the force sensor that uses the signal to alter an operation of the electronic device. The device can, in one embodiment, be worn by a user.

In another aspect, a method for determining a change in a pressure differential across a pressure sensitive surface having a surface area and carried by a housing of an electronic device is described. The method is carried out by detecting a magnitude of a force applied at the pressure sensitive surface by a force sensor carried by the housing, measuring the magnitude of the applied force over a duration of time, and determining a leak rate based upon a difference in the measured magnitude over the period of time.

In another aspect, a wearable electronic depth gauge includes at least a housing having walls that define an internal volume and that comprises a reference pressure datum, a pressure sensitive surface carried by the housing having an exterior surface having a surface area that receives an external pressure from an external environment, an extended range force detector positioned with respect to the pressure sensitive surface and the housing such that the extended range force detector is configured to detect a force corresponding to the external pressure. In response to the detecting of the force, the extended range force detector provides a single signal indicating a magnitude of the detected force at a first sensitivity level when the magnitude is below a threshold level and at a second sensitivity level when the magnitude is at or above the threshold level. The wearable depth gauge also includes a processor carried by the housing that receives the signal and uses the surface area and the magnitude of the detected force to derive the external pressure that the processor compares to the reference pressure datum to provide a pressure differential corresponding to a depth of water.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The disclosure will be readily understood by the following detailed description in conjunction with the accompanying drawings, wherein like reference numerals designate like structural elements, and in which.

Figure 1:
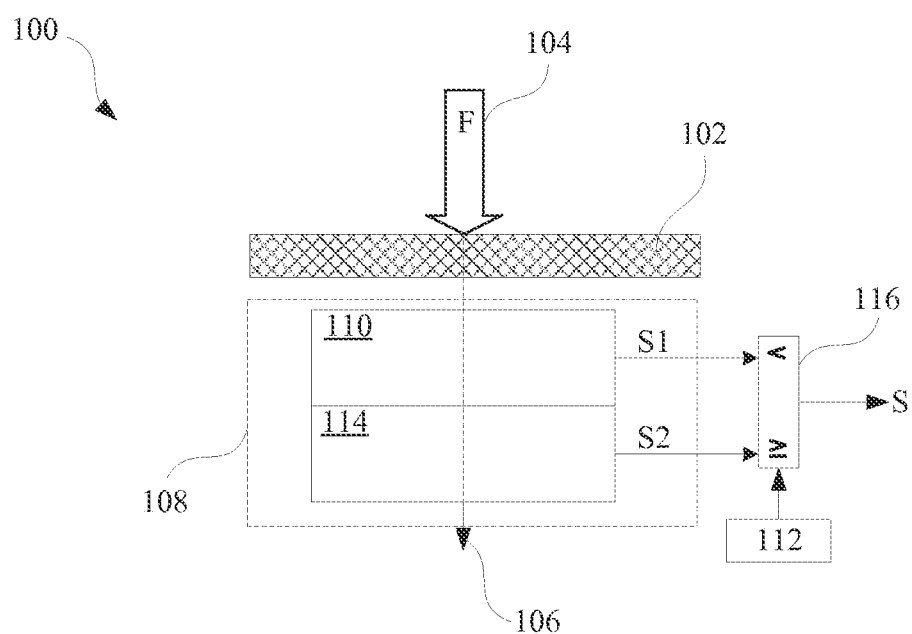
FIG. 1 illustrates a representative extended range force sensor in accordance with the described embodiments.

Those skilled in the art will appreciate and understand that, according to common practice, various features of the drawings discussed below are not necessarily drawn to scale, and that dimensions of various features and elements of the drawings may be expanded or reduced to more clearly illustrate the embodiments of the present invention described herein.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting such that other embodiments may be used, and changes may be made without departing from the spirit and scope of the described embodiments.

The following disclosure relates to an electronic device. In particular, the electronic device can have a form factor that renders the electronic device wearable. By wearable, it is meant that a user can wear the electronic device as a decorative (but also functional) accessory that can be secured or otherwise attached to a garment or appended to a user's limb much like a watch. In the context of this discussion, however, the electronic device can be considered an accessory that can be carried or worn by the user. In this way, the electronic device can be act both as an adornment as well as a source of useful information. The information can be provided real time and can be associated with a current physical state of the user and/or information regarding an external environment that the user would find of interest. For example, the electronic device can be worn as a bracelet or a watch that can be taken along on various athletic endeavors such as rock climbing, skydiving, scuba diving, jogging etc. In this way, the electronic device can be used to monitor (and record if need be) external conditions such as temperature, pressure, light conditions, speed, distance and so on.

A particularly useful, but by no means only, use of the electronic device is one in which the electronic device measures an ambient pressure. This is particularly important for divers and more specifically scuba divers that must know a precise dive depth, as depth dictates a manner of ascent and duration of time for ascent. However, in order to accurately monitor pressure changes, especially pressure changes associated with underwater activity, the electronic device must be able to detect a wide range of pressure with a degree of accuracy that can be maintained regardless of the immediate pressure. For example, in order to avoid any pressure related medical issues, the diver using underwater equipment that regulates the pressure of air being breathed must know within a few feet a true depth under water as it is that pressure that the underwater equipment uses to set the pressure of the air being breathed. This is particularly important since it is the relative change in pressure that must be taken into consideration when ascending. Therefore, in order for the electronic device to be used as a depth gauge when carried by the user underwater, the electronic device must be capable of detecting the ambient water pressure over an extended range operable with an acceptable level of sensitivity to pressure changes. By sensitivity, it is meant a relationship between a changes in output compared to a change of input. In the case of a force sensor, the sensitivity can be defined along the lines of Eq. (1) below:

$$\text{Sensitivity} \propto \Delta S / \Delta F \qquad \text{Eq. (1)}$$

representing a change in output signal S and applied force F.

Accordingly, the following provides a description of an electronic device and more particularly, a force detector that is capable of detecting a static force over an extended range having a known level of sensitivity over the extended range. In another embodiment, the force sensor can be used in a dynamic mode of operation to test for seal integrity. In other words, the force sensor operable in the dynamic mode can be used to perform a leak analysis and detection. Accordingly, a testing method and protocol can be achieved that allows electronic devices having a water (or other fluid) resistant enclosure to be tested using an internal force sensor over a period of time. A change in a magnitude of a detected force can be used to determine 1) that a leak is present, 2) a leak rate associated with the leak, and 3) a characteristic of the leak (i.e., if the leak rate is constant or varies in accordance with an internal pressure and so on).

It should be noted that pressure can be directly related to an applied force simply by determining an area over which the force is applied in accordance with Eq. (2) below:

$$F = P \times A; \qquad \text{Eq. (2)}$$

F is applied force
P is pressure; and
A is area over which force F is applied.

In general, force F can be a function of time meaning that over a period of time a magnitude of force F can vary. However, in a generally static configuration, force F is essentially constant (or varies less than a pre-determined amount) over a prescribed period of time. In a generally dynamic configuration (such as a testing of hermetic integrity of an enclosure), force F can vary in time in accordance with a leak rate and/or a leak characteristic.

The embodiments shown and described relate to an electronic device. The electronic device can take the form of a wearable electronic device that can be attached to a garment worn by a user or carried with respect to an appendage (such as a wrist) of the user. These and other embodiments are discussed below with reference to FIGS. 1-10. However, those skilled in the art will readily appreciate that the detailed description given herein with respect to these Figures is for explanatory purposes only and should not be construed as limiting. It should be noted that in the following discussion, a notation of force is expressed in terms of mass-equivalent force according to a standard conversion that one newton (NT) is about equivalent to 100 grams and 1 kg is about equivalent to 10 NT.

FIG. 1 shows a representation of system 100 in accordance with the described embodiments. System 100 can include force transmissive surface 102 that is capable of transmitting force 104 along force (or load) path 106 that includes force sensor system 108 configured to sense force 104 in terms of both a magnitude and a duration. By force transmissive it is meant that a force applied to force transmissive surface can be transmitted substantially unaffected. For example, force transmissive surface 102 can move in accordance with a force applied such that the applied force is transmitted to a force sensor, for example. It should be noted that force 104 can be considered to be a static force in some embodiments and a dynamic force in other embodiments. For example, in order to determine if a leak is present, the force considered is a dynamic force (in that the force can vary over time) whereas a static force is one that is essentially a dynamic force. In this regard, for a static force, force sensor system 108 can be based upon, for example, a capacitance type force detector that relies upon a change in capacitance associated with capacitively coupled structures. For example, a change in the capacitance can be brought about by a change in distance between two charged plates caused by the application of force 104. The change in capacitance can then be used to calculate a corresponding magnitude of force 104. Another useful type of force sensor is a strain gauge type force sensor. A strain gauge takes advantage of the physical property of electrical conductance and its dependence on the conductor's geometry and is therefore well suited for sensing a static load. With the strain gauge type force sensor, the applied force deforms a deformable structure (such as a resistor) and the strain gauge then measures the deformation (strain) as a change in electrical resistance. This change in electrical resistance can then be used as a measure of the strain and hence the applied force. In some embodiments, a load cell can be useful. As such, a load cell can include a number (such as four) of strain gauges that are electrically coupled together using a bridge (such as a Wheatstone bridge) formation that provides an output signal that can be used to calculate the applied force. It should be further noted that even though piezoelectric based sensors are precise and rugged, a piezoelectric based force sensor is not well suited for detection and measurement of a static load as the static load represents a steady state environment that would result in a constant loss of electrons and a concomitant loss of sensitivity.

Referring again to FIG. 1, force sensor system 108 can be capable of detecting a magnitude of force 104 over an extended range that can be divided into sub-ranges each having a corresponding level of sensitivity. For example, force sensor system 108 can detect force 104 having a magnitude that ranges from about null (or nominal) to a first threshold level and provide a first output signal corresponding to a first sensitivity level. Force sensor system 108 can also detect force 104 having a magnitude up to and including a second threshold level that is greater than the first threshold level and provide a second output signal corresponding to a second sensitivity level. For example, force sensor system 108 can detect force 104 in the range of about zero to about 500 grams corresponding to a first (low) range and provide an output signal corresponding to the low range and having a low range sensitivity level. However, when force 104 is at or above the first threshold (that defines a transition to a second (high) range), force sensor system 108 can continue to provide the output signal corresponding to the high range and having a high range sensitivity level.

In a particular embodiment, force sensor system 108 can include component force sensors configured for sensing force 104 in specific sub-ranges and provide an output signal for the appropriate sub-range having a sub-range level of sensitivity. Accordingly, force sensor system 108 can include first force sensor 110 arranged to detect force 104 and provide output signal S1 corresponding to a first sensitivity level up to first threshold level 112. In some cases, first threshold level 112 can correspond to a saturation level of first force sensor 110. By saturation level it is meant that at or above the saturation level, the sensitivity of first force sensor 110 drops precipitously as any increase in force is not generally reflected in output signal S1. Second force sensor 114 can be used to detect a magnitude of force 104 that is greater than or equal to first threshold level 112 and as such provide output signal S2 corresponding to a second sensitivity level. In one embodiment, first force sensor 110 and force sensor 114 are each in communication with selector 116 arranged to select either signal S1 or signal S2 based upon a determination of the sub-range corresponding to the magnitude of force 104. For example, if the magnitude of force 104 is determined to be within the second sub-range, then selector 116 will select output signal S2 for outputting, otherwise, signal S1 is selected for outputting. As shown in FIG. 1, force path 106 can include force sensors 110 and 114 coupled in a serial arrangement by which it is meant that each sensor experiences the same magnitude and duration of force 104. It should be noted that force sensors 110 and 114 could also be coupled in a parallel arrangement in which each sensor detects a different proportional force or a combination of parallel and serial.

Figure 2:
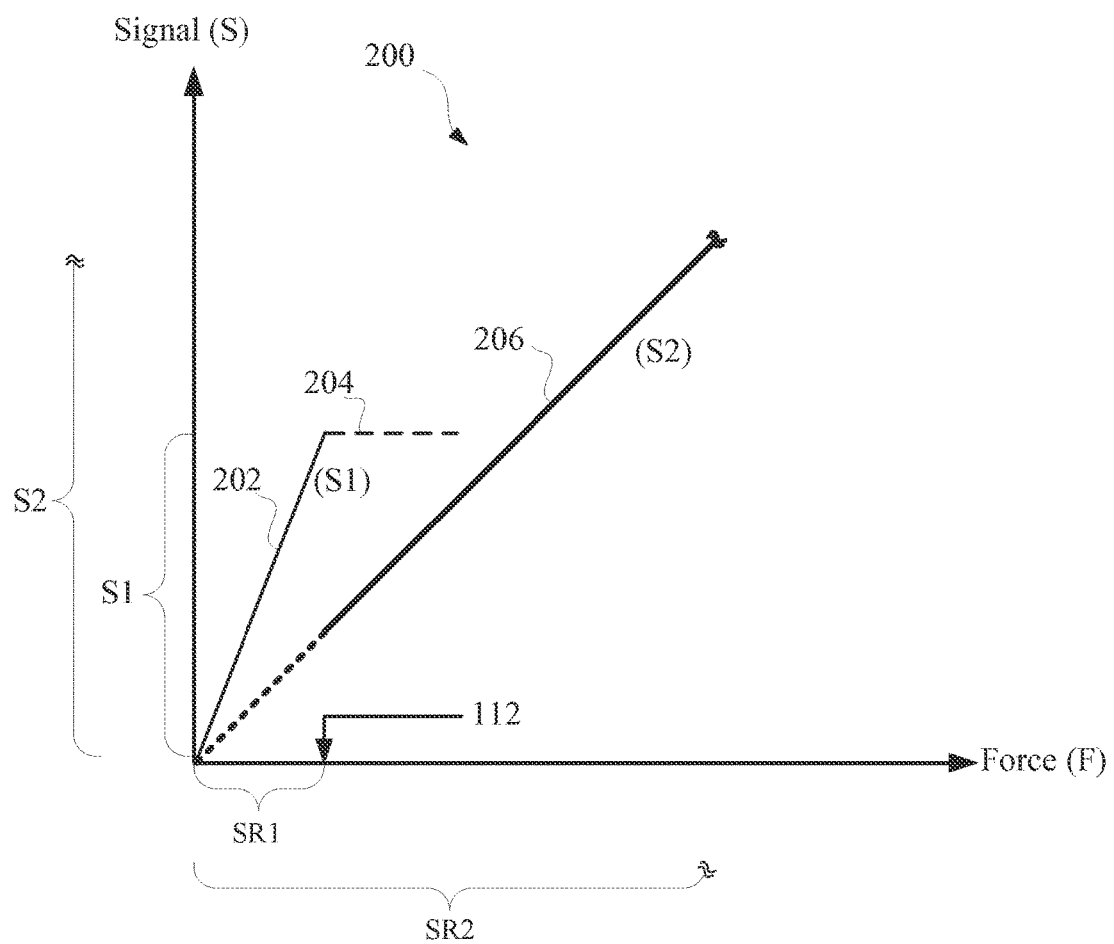
FIG. 2 illustrates graph showing a relationship of the performance metrics of a first force sensor and a second force sensor in accordance with the described embodiments.

FIG. 2 illustrates graph 200 showing a relationship of the performance metrics of first force sensor 110 and second force sensor 114 in accordance with the described embodiments. The performance metrics of each of the force sensors is demonstrated as a response curve vs. applied force relationship. In this embodiment, the response curves are shown to be linear for sake of simplicity and clarity, but of course, the response curves can be any shape appropriate for the particular sensors at hand. Accordingly, the X-axis represents force 104 applied to force transmissive surface 102 whereas the Y-axis represents the output signal corresponding to each of the force sensors. More specifically, first force sensor 110 can be represented by a linear relationship represented by line 202 that shows the relationship between output signal S1 and applied force 104 in force sub-range SR1 that extends from about null (or zero) to first threshold level 112. In the embodiment shown, first threshold level 112 corresponds to saturation level 204 by which it is meant that any further increase in force 104 at first force sensor 110 will generally not result in a corresponding change in output signal S1. Moreover, second force sensor 114 can be represented by a linear relationship represented by line 206 (it should be noted that the dotted line represents a change of scale in force 104) that shows the relationship between output signal S2 and applied force 104 in force sub-range SR2 that extends from about null (or zero) to a second threshold level (not shown) that can also correspond to a saturation level of second force sensor 114 by which it is meant that any further increase in force 104 at second force sensor 114 will generally not result in a corresponding change in output signal S2.

Figure 3:
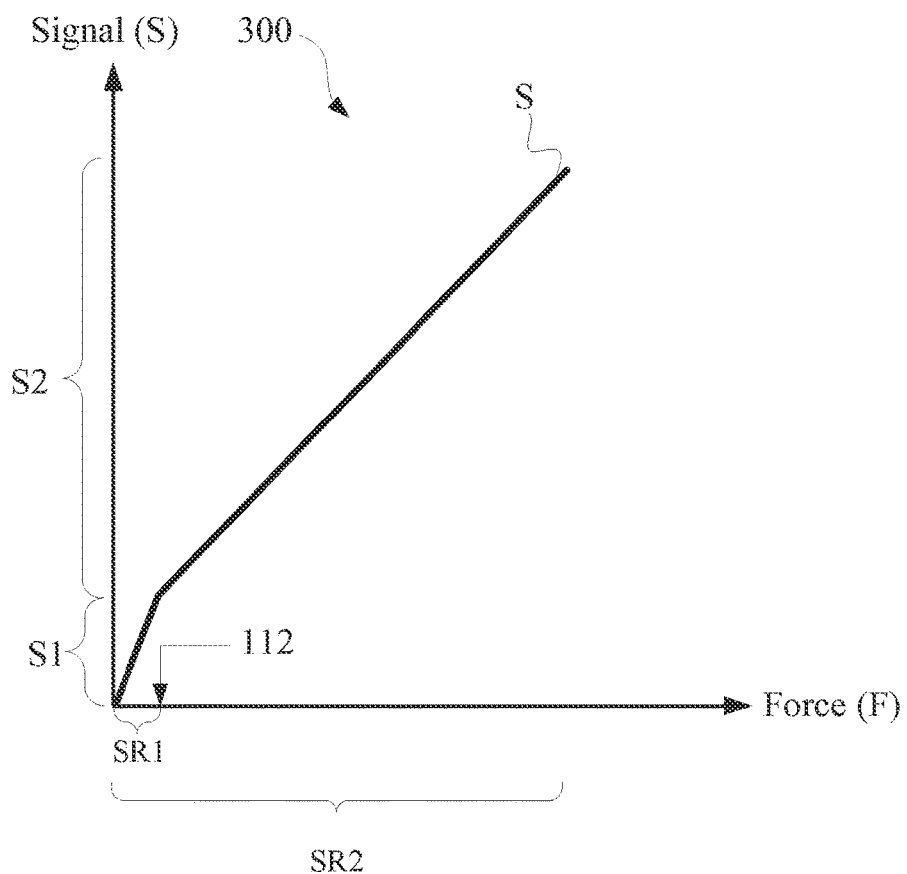
FIG. 3 illustrates a graph showing output signal S from a force sensor as function of force F in accordance with the embodiments shown in FIG. 2.

FIG. 3 illustrates graph 300 showing output signal S from force sensor system 108 as function of force F in accordance with the embodiments shown in FIG. 2. As shown, output signal S can be represented by a continuous function corresponding to output signal S1 having a first sensitivity level in sub-region SR1 that transitions to output signal S2 having a second sensitivity level in sub-region SR2. In the described embodiment, threshold limit 112 provides a break point between output signal S1 and output signal S2 and represents a transition between sub-regions R1 and R2. Accordingly, as force 104 increases from a first magnitude within sub-region SR1, force sensor system 108 can output signal S1 having a level of sensitivity corresponding to sub-region SR1. As the magnitude of force 104 increases reaching first threshold 112 (that can correspond to a saturation level of first force sensor 110), force sensor system 108 transitions to providing output signal S2 having a sensitivity level corresponding to sub-region SR2. In this way, force sensor system 108 can provide consistent force magnitude information at correspondingly consistent level of sensitivity over an extended range of force magnitude.

Figure 4:
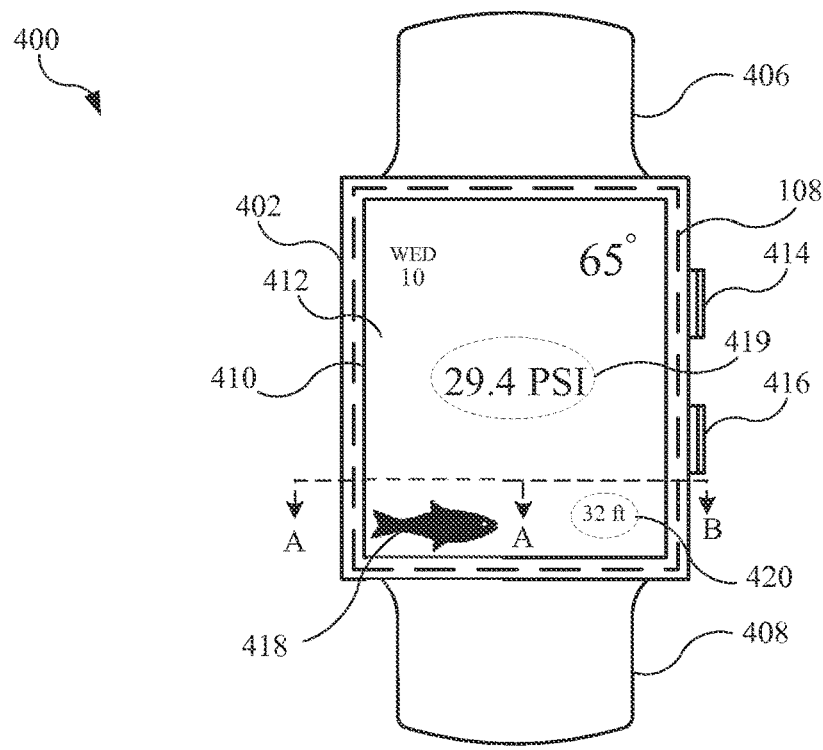
FIG. 4 illustrates a front view of an electronic device in accordance with the described embodiments.

FIG. 4 illustrates a front view of an embodiment of an electronic device 400, in accordance with the described embodiments. In some embodiments, the electronic device 400 is a mobile communication device, such as a smart phone. In other embodiments, the electronic device 400 is a wearable computing device. In the embodiment shown in FIG. 4, the electronic device 400 is a wearable electronic device designed to secure with an appendage (for example, an arm or a leg) of a user of the electronic device 400.

Electronic device 400 may include an enclosure 402 formed from a rigid material, such as a metal (including stainless steel or aluminum). The enclosure 402 may be coupled with a first band feature 406 and a second band feature 408, with the first band feature 306 and the second band feature 408 are designed to secure the electronic device 400 with an appendage of a user. Also, the electronic device 400 may include a display module 410 designed to display visual content, including a day and a time of the day. In some embodiments, the display module 410 is a light-emitting diode ("LED") display. Further, in some embodiments, the display module 410 is an organic light-emitting diode ("OLED") display. The display module 410 may further include a cover glass 412 disposed over the display module

410. In addition to displaying time, the display module 410 may also display visual content based upon applications, or "apps," stored on a memory circuit (not shown) disposed between the enclosure 402 and the display module 410. For example, icon 418 can be used to indicate a particular athletic activity (in this case a marine animal can indicate aquatic activity such as fishing or diving). Other related icons can include icon 419 showing an ambient pressure and icon 420 can show depth underwater based upon input from sensor 108 carried by housing 402 (indicated by dotted line). In this embodiment, sensor 108 can be carried by housing 402 along an entire perimeter of housing 402 at an interface between housing 402 and display module 410. In this way, sensor 108 can provide accurate pressure sensor data (based upon force applied to display module 410) but can also provide a good environmental seal isolating an interior of electronic device 400 from an external environment. In this way, the interior of electronic device 400 can act as an environmental reference datum. For example, the interior of electronic device 400 can include air at one atmosphere of pressure. In this, way a pressure differential across cover glass 412 can represent an ambient pressure that can correspond to a depth underwater. Also, the electronic device 400 may pair, via wireless communication, with an additional electronic device (not shown), such as a smart phone.

The electronic device 400 may include several input features electrically coupled with one or more processors (not shown), and designed to control the display module 410. For example, as shown in FIG. 4, the electronic device 400 includes a first control input 414 and a second control input 416, each of which may be partially disposed in openings of the enclosure 402. The first control input 414 may take the form of a dial design for clockwise and counter-clockwise rotation, with the rotation used to control the display module 410. Further, the first control input 414 may be depressed to define a further control input feature. The second control input 416 may take the form of a button that provides an additional control input feature when depressed. Although not shown, the first control input 414 and/or second control input 416 may be disposed in other locations of the enclosure 402. Also, the electronic device 400 may include more or fewer control inputs in other embodiments. Further, the electronic device 400 may include a touch sensor (not shown) disposed behind (and in some cases integrated) with the display module 410. This allows the user to further control the display module 410 by depressing the cover glass 412 triggering the touch sensor to generate a control input and alter the visual content of the display module 410.

Figure 5:
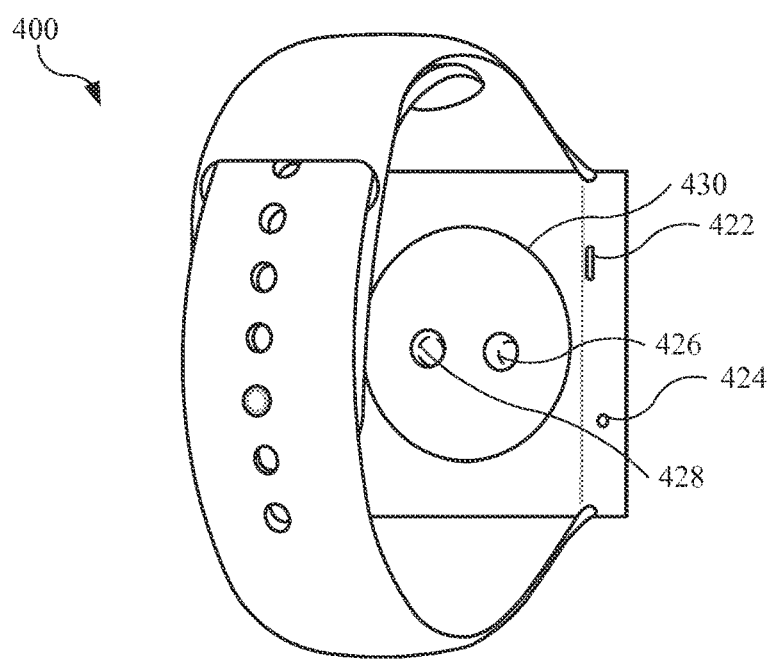
FIG. 5 illustrates a rear view of the electronic device shown in FIG. 4, showing several openings in the enclosure.

FIG. 5 illustrates a rear view of the electronic device shown in FIG. 4, showing several openings in the enclosure 402. As shown, the first band feature 406 is engaged with the second band feature 408 to define a closed configuration allowing the electronic device 400 to be secured with an appendage of a user. The electronic device 400 may include a first opening 422 in the enclosure 402 that may allow, for example, an output of audible sound from a speaker module (not shown) disposed in the enclosure 402. Also, the electronic device 400 may include a second opening 424 in the enclosure 402 that may allow, for example, an input of audible sound to a microphone (not shown) disposed in the enclosure 402. Although the first opening 422 and the second opening 424 are shown in distinct locations, the first opening 422 and the second opening 424 may vary in location along the enclosure 402, and further, may vary in size and shape. Further, the number of openings may vary according to the functionality of the electronic device 400. For example, an additional opening (not shown) may be used in conjunction with the first opening 422 to enhance the audible sound.

The electronic device 400 shown in FIG. 4 may include additional features. For example, the electronic device 400 may include a light source 426 designed to emit light in the form of light pulses. In some embodiments, the light source 426 includes a light-emitting diode ("LED"). Further, in some embodiments, the light source 426 includes a generally green color. Also, the electronic device 400 may include a sensing element 428 designed to sense light from the light source 426 that is reflected by, for example, a user wearing the electronic device 400. Accordingly, in some embodiments, the sensing element 428 is a photoelectric sensor or photodiode. Although a single light source and a single sensing element are shown, other embodiments may include two or more light sources as well as two or more sensing elements. Also, a cover 430, formed from a material such as glass or crystal, may overlay the light source 426 and the sensing element 428, with the cover 430 being transparent in locations corresponding to the light source 426 and the sensing element 428.

Figure 6:
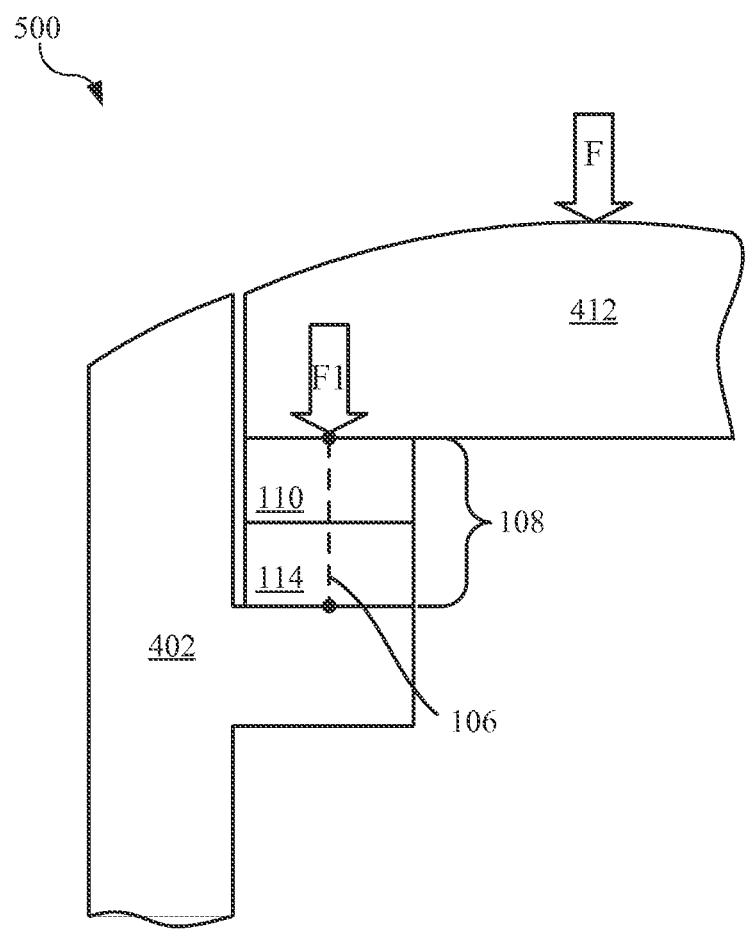
FIG. 6 illustrates a cross sectional view of the electronic device shown in FIG. 4, taken along line A-A.

FIG. 6 illustrates a cross sectional view of the electronic device 400 shown in FIG. 4, taken along line A-A. In particular, sensor 108 is carried by housing 402 such that sensor 108 located along force path 106 that includes cover glass 412. In the described embodiment, sensor 108 can further include first force sensor 110 and second force sensor 114 coupled in series with each other. In this way, force F1 (a proportion of force F applied at cover glass 412) can be detected by sensor 108 that can, in turn, respond by providing signal S that can indicate a magnitude of force F1. In the case where electronic device 400 is configured to respond along the lines of a depth gauge, signal S can be used by a processor carried by housing 402 to determine a current depth under water of electronic device 400 that can be displayed by display module 410. It should be noted that sensor 108 could also respond to a negative pressure differential (in which the external pressure is less than an internal pressure reference datum) and provide act as an altimeter. In any case, since an interior of electronic device 400 is sealed from an external environment by sensor 108 (in addition to or in place of a separate environmental seal), the interior of electronic device 400 can include a volume of air (or other gas) that can act as the internal pressure reference datum. In this case, the internal pressure datum can be maintained at about an STP condition of one atmosphere. In this way, the pressure reading presented by display module 410 can be read as either absolute pressure (including standard atmosphere) or as a relative pressure (a pressure differential).

Figure 7:
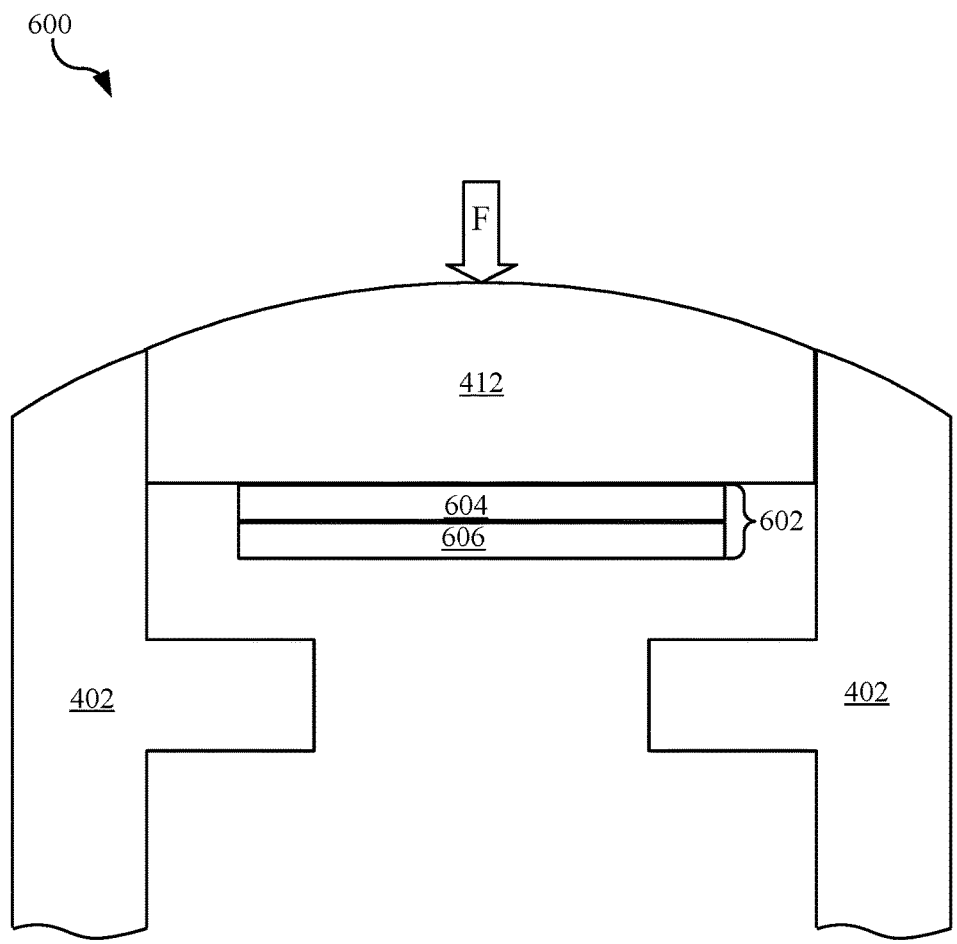
FIG. 7 shows another embodiment of force sensor in form of a strain gauge.
Figure 8:
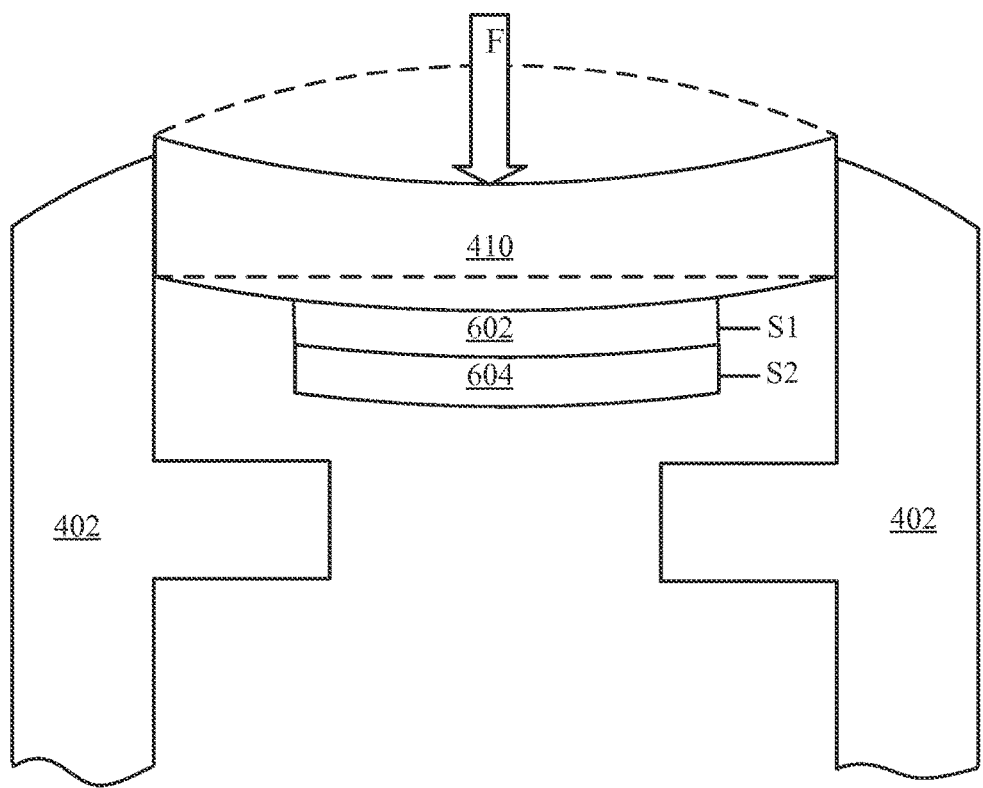
FIG. 8 shows the strain gauge of FIG. 7 in a deflected configuration in response to force applied force F.

FIG. 7 shows another embodiment 600 of force sensor system 108 in form of strain gauge 602. In this arrangement, force sensor system 108 can be used to determine a force directly applied to cover glass 412 by an amount of deflection of cover glass 412. It should be noted that force sensor system 108 can be positioned at specific locations and can therefore be used as a form of touch/pressure input as well as provide a mechanism for determining an overall pressure exerted on cover glass 412. It should be noted that as shown in FIG. 8, strain gauge 602 could include a deformable resistive element that can be used to detect and evaluate a magnitude of force F by virtue of a deformation of the resistive element. The resistive element can be physically secured to an underside of cover glass 412 (as shown in FIG. 8). However, the resistive element can also be incorporated within cover glass 412, or in those situations where cover glass 412 includes a number of layers in a stacked arrangement, the resistive element can be disposed within the layered stack. The resistive elements can also be discreet and separate and located at specific locations that can be used to detect a stress event. For example, the resistive elements can be located a corner and as such can be useful in detection of a drop event. In any case, the deformation of cover glass 412 can be associated with a discreet event such as a finger press or as a pressure event that affects substantially all of an exterior surface of cover glass 412. In any case, FIG. 8 illustrating deformation of cover glass 412 along line A-B in response for force 104 being applied thereto. Strain gauge 602 can further include first strain gauge 604 coupled in series with second strain gauge 606 that can cooperate to provide output signal S over an extended range of applied force 104.

Figure 9:
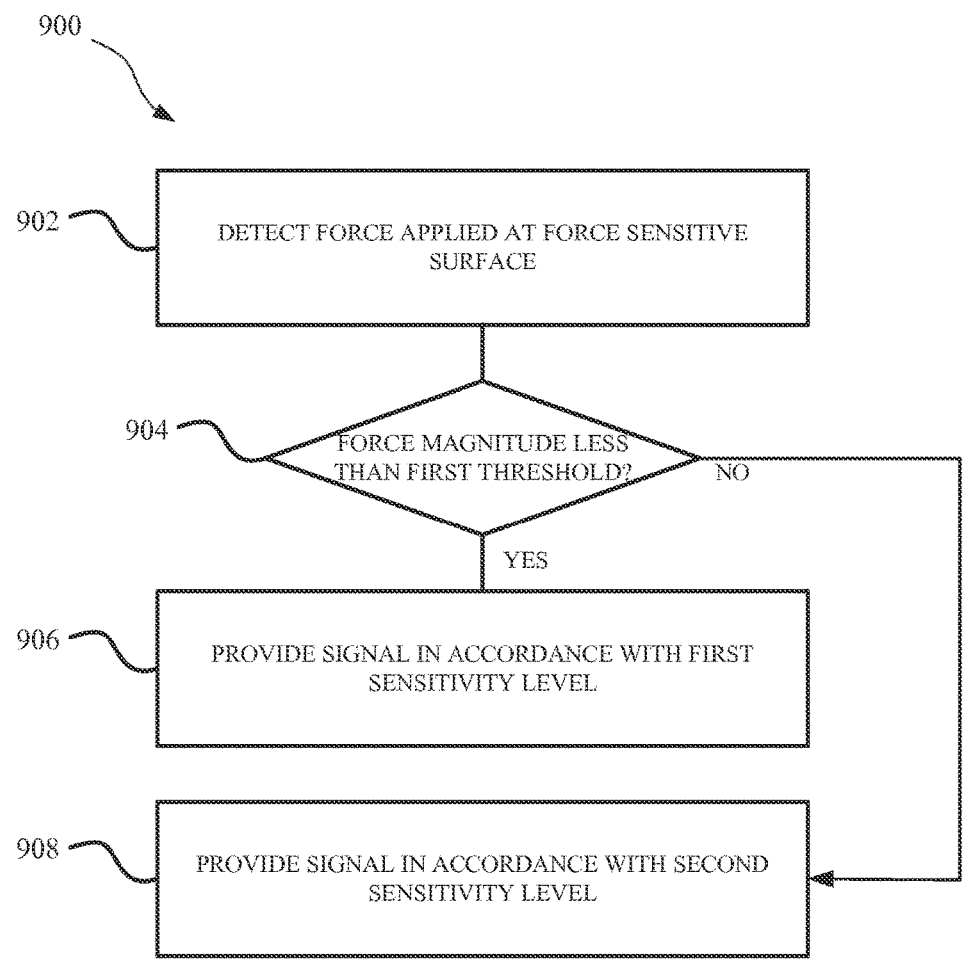
FIG. 9 illustrates a flowchart showing a method for preventing ingress of a water-based solution to a component in an electronic device, in accordance with the described embodiments.

FIG. 9 illustrates a flowchart 900 showing a method for using a wearable electronic device as a pressure detector in accordance with the described embodiments. Process 900 can be carried out by detecting a force applied to a force transmissive surface at 902. At 904, a determination is made whether or not magnitude of the force detected at 902 is less than a first threshold level. If it is determined that the detected force is less than the first threshold, a signal in accordance with a first sensitivity level is provided at 906, otherwise, a signal is provides in accordance with a second sensitivity level different than the first sensitivity level at 908.

Figure 10:
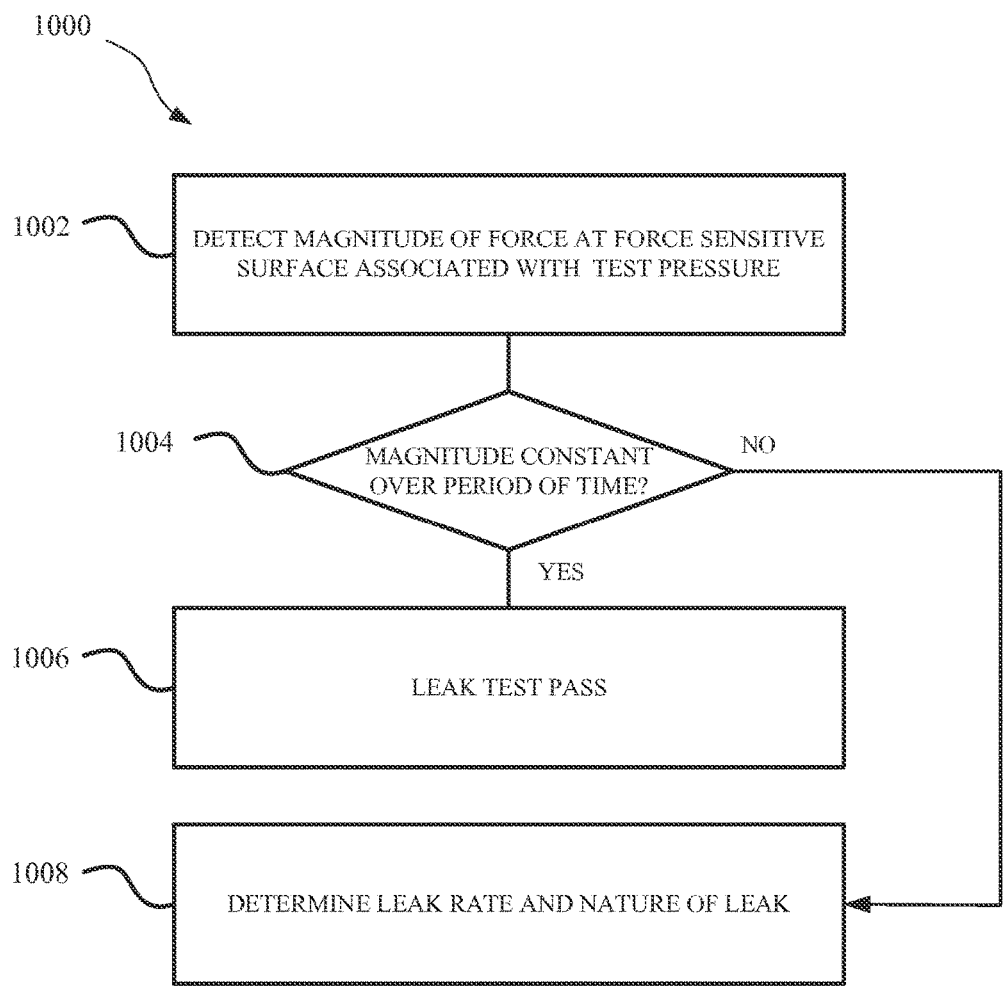
FIG. 10 illustrates a flowchart showing a leak test process in accordance with the described embodiments.

FIG. 10 illustrates a flowchart showing a leak test process 100 in accordance with the described embodiments. In particular, the leak test process 1000 can be carried out by exposing a hermetically sealed enclosure to a pressure differential between an internal pressure at an interior of the enclosure and an external pressure at an exterior of the enclosure. In one situation, the pressure differential can be positive meaning that the external pressure is greater than the internal pressure. Alternatively, the pressure differential can be negative in that the internal pressure is greater than the external pressure. This variation in leak testing protocol can be useful in detecting specific leak mechanisms. For example, exposing the enclosure to a positive pressure differential can be useful in evaluating an environmental seal design to prevent ingress of fluid to an interior of the enclosure. This is particularly useful for evaluating seals used to prevent ingress from openings in a housing (such as those used for connectors, audio jacks, and so on).

In any case, process 1000 can be carried out by detecting a magnitude of force associated with a test pressure applied to a force transmissive surface at 1002. It should be noted that the test pressure could create either a positive or negative pressure differential across the force transmissive surface depending upon specifics of the test being performed. The medium by which the force is generated can include, for example, a gas or a liquid, and can be consistent with an expected leakant. For example, if the enclosure is anticipated for use underwater, than the testing medium can be water. If the enclosure is anticipated for use as altimeter, then the testing medium can be air. In any case, at 1004, a determination is made whether or not magnitude of the force detected at 1002 is varying in over a pre-determined amount of time. If it is determined that magnitude of the detected force is not varying (or varying less than a pre-determined amount) then at 1006, the enclosure can be said to have passed the leak test. Alternatively, if the magnitude of the detected force is determined to vary in time (or varying greater than or equal to the pre-determined amount) then at 1008, a leak rate is determined.

Figure 11:
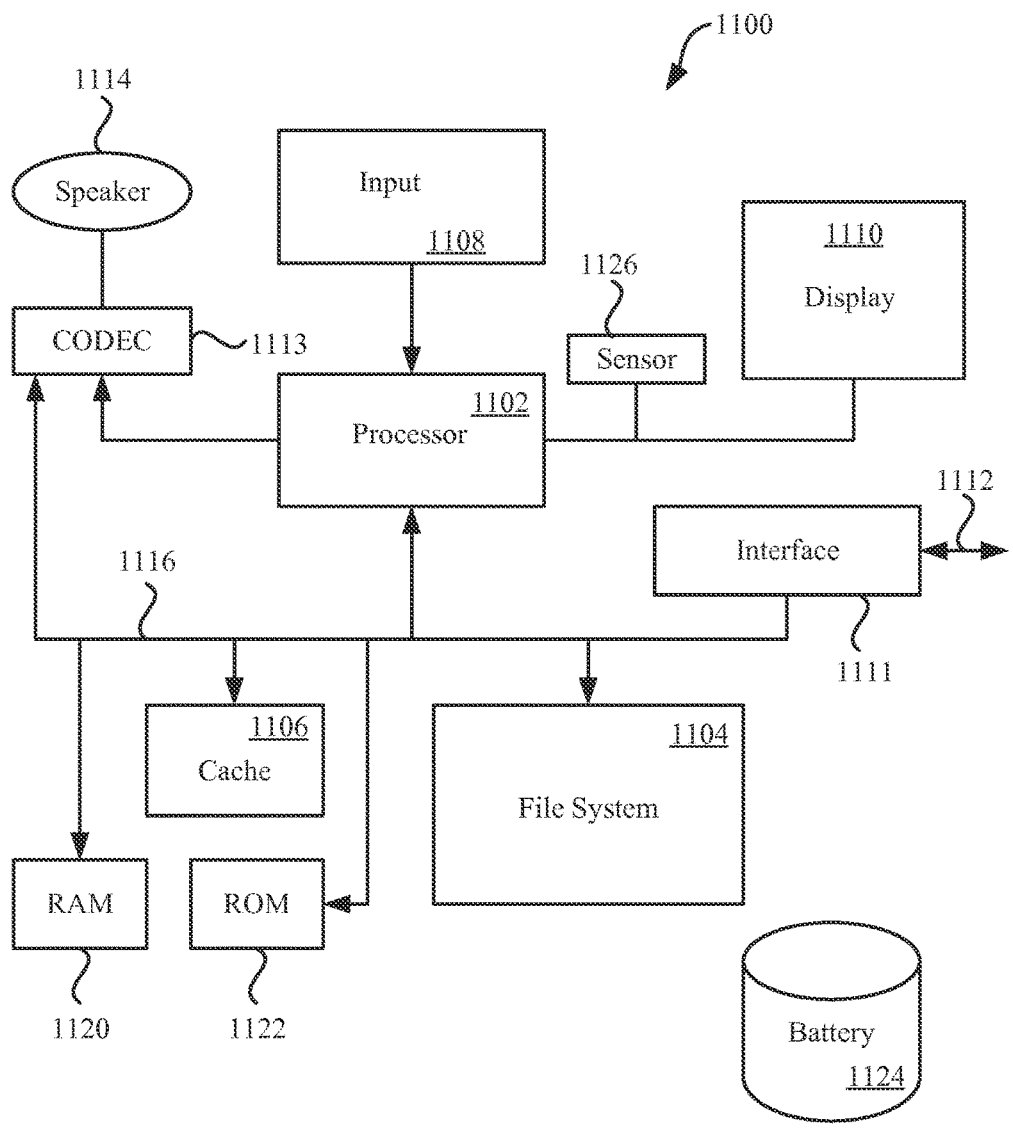
FIG. 11 is a block diagram of an electronic device suitable for use with the described embodiments.

FIG. 11 is a block diagram of an electronic device 1100 suitable for use with the described embodiments. The electronic device 1100 illustrates circuitry of a representative computing device. The electronic device 1100 includes a processor 1102 that pertains to a microprocessor or controller for controlling the overall operation of the electronic device 1100. The electronic device 1100 stores media data pertaining to media items in a file system 1104 and a cache 1106. The file system 1104 is, typically, a semiconductor memory, cloud storage, or storage disks or hard drives. The file system 1104 typically provides high capacity storage capability for the electronic device 1100. However, since the access time to the file system 1004 is relatively slow, the electronic device 1100 can also include a cache 1106. The cache 1106 is, for example, Random-Access Memory (RAM) provided by semiconductor memory. The relative access time to the cache 1106 is substantially shorter than for the file system 1104. However, the cache 1106 does not have the large storage capacity of the file system 1104. Further, the file system 1104, when active, consumes more power than does the cache 1106. The power consumption is often a concern when the electronic device 1100 is a portable media device that is powered by a battery 1124. The electronic device 1100 can also include a RAM 1120 and a Read-Only Memory (ROM) 1122. The ROM 1122 can store programs, utilities or processes to be executed in a non-volatile manner. The RAM 1120 provides volatile data storage, such as for the cache 1106.

The electronic device 1100 also includes a user input device 1108 that allows a user of the electronic device 1100 to interact with the electronic device 1100. For example, the user input device 1108 can take a variety of forms, such as a button, keypad, dial, touch screen, audio input interface, visual/image capture input interface, input in the form of sensor data, etc. Still further, the electronic device 1100 includes a display 1110 (screen display) that can be controlled by the processor 1102 to display information to the user. A data bus 1116 can facilitate data transfer between at least the file system 1104, the cache 1106, the processor 1102, and the CODEC 1113.

In one embodiment, the electronic device 1100 serves to store a plurality of media items (e.g., songs, podcasts, etc.) in the file system 1004. When a user desires to have the electronic device play a particular media item, a list of available media items is displayed on the display 1010. Then, using the user input device 1008, a user can select one of the available media items. The processor 1002, upon receiving a selection of a particular media item, supplies the media data (e.g., audio file) for the particular media item to a coder/decoder (CODEC) 1013. The CODEC 1013 then produces analog output signals for a speaker 1014. The speaker 1014 can be a speaker internal to the electronic device 1100 or external to the electronic device 1100. For example, headphones or earphones that connect to the electronic device 1100 would be considered an external speaker.

The electronic device 1100 also includes a network/bus interface 1111 that couples to a data link 1012. The data link 1112 allows the electronic device 1100 to couple to a host computer or to accessory devices. The data link 1112 can be provided over a wired connection or a wireless connection. In the case of a wireless connection, the network/bus interface 1111 can include a wireless transceiver. The media items (media assets) can pertain to one or more different types of media content. In one embodiment, the media items are audio tracks (e.g., songs, audio books, and podcasts). In another embodiment, the media items are images (e.g., photos). However, in other embodiments, the media items can be any combination of audio, graphical or visual content. Sensor 1126 can take the form of circuitry for detecting any number of stimuli. For example, sensor 1126 can include a Hall Effect sensor responsive to external magnetic field, an audio sensor, a light sensor such as a photometer, and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A wearable electronic device, comprising:
   a housing that defines an internal volume;
   a display module;
   a cover glass coupled with the housing and covering the display module, the cover glass defining a force transmissive surface capable of receiving a force;
   a force sensor system located in the internal volume between the cover glass and the housing, the force sensor system configured to sense the force received from the force transmissive surface, the force causing the cover glass to move relative to the housing, wherein the force sensor system comprises:
      a first force sensor that provides a first signal in accordance with a first sensitivity level, and
      a second force sensor that provides a second signal in accordance with a second sensitivity level different from the first sensitivity level.

2. The wearable electronic device as recited in claim 1, further comprising:
   an output circuit in communication with the first force sensor and the second force sensor that selects for outputting only the first signal when the force is less than a threshold level and selects for outputting only the second signal when the force is greater than or equal to the threshold level.

3. The wearable electronic device as recited in claim 1, wherein the threshold level corresponds to a saturation level of the first force sensor.

4. The wearable electronic device as recited in claim 1, wherein the first force sensor is stacked over the second force sensor in a serial arrangement.

5. The wearable electronic device as recited in claim 1, wherein the first force sensor and second force sensor are coupled in a parallel arrangement.

6. The wearable electronic device as recited in claim 1, wherein the force sensor system comprises two plates, and wherein the forces causes a change in a distance between the two plates that changes the capacitance generated by the force sensor system, the capacitance corresponding to a measure of the force.

7. The wearable electronic device as recited in claim 1, wherein the force sensor system comprises a strain gauge coupled to the cover glass, the strain gauge configured to deform in response to the force.

8. The wearable electronic device as recited in claim 1, wherein the force applied at the force transmissive surface corresponds to a pressure exerted at an exterior of the force transmissive surface.

9. The wearable electronic device as recited in claim 8, wherein when a pressure differential between the pressure at the exterior of the force transmissive surface and an internal reference pressure datum is positive, then the applied force is compressive, otherwise, the pressure differential is negative and the applied force is tensile.

10. The wearable electronic device as recited in claim 1, further comprising:
    a first band feature coupled to the housing; and
    a second band feature coupled to the housing, wherein the first band feature combines with the second band feature to secure the housing with a user.

11. An electronic device, comprising:
    a housing having walls that define an internal volume and that comprises a reference pressure datum;
    a pressure sensitive surface defined by a transparent cover that is carried by the housing having an exterior surface having a surface area that receives an external pressure from an external environment;
    a display module covered by the transparent cover;
    a capacitive force detector having a first sensitivity level and a second sensitivity level, the capacitive force detector positioned with respect to the pressure sensitive surface and the housing such that the capacitive force detector is configured to detect a force corresponding to the external pressure and in response to the detecting of the force, provide a single signal in accordance with the first sensitivity level of the capacitive force detector when a magnitude of the force is below a threshold level and provide the single signal in accordance with the second sensitivity level of the capacitive force detector when the magnitude is at or above the threshold level; and
    a processor carried by the housing that receives the single signal and uses the surface area and the magnitude of the force to derive the external pressure that the processor compares to the reference pressure datum to provide a pressure differential corresponding to a depth of water, the pressure differential being presented on the display module.

12. The electronic device as in claim 11, wherein the capacitive force sensor hermetically seals the internal volume from the external environment.

13. The electronic device as recited in claim 11, wherein the threshold level is about 5N.

14. The electronic device as recited in claim 11, wherein the capacitive force detector comprises:
    a first capacitive force sensor coupled to the transparent cover, the first capacitive force sensor providing a first signal in accordance with the first sensitivity level in response to detection of the force; and
    a second capacitive sensor coupled to capacitive force sensor and the housing, the second capacitive force sensor providing a second signal in accordance with the second sensitivity level.

15. A wearable electronic device, comprising:
    a housing comprising a side wall that defines a full front opening characterized as having a perimeter, the housing further comprising a flange extended internally from the side wall along the perimeter;
    a display module positioned within the full front opening and being supported by the flange, the display module having a cover glass disposed thereon;

a sensor assembly carried by the flange and positioned at an interface between the display module and the flange, wherein the sensor assembly comprising a force sensor that is capable of detecting a force exerted on the cover glass and produce a signal with a value that is commensurate with a magnitude of the force; and a processor carried by the housing, wherein the processor is capable of determining an ambient pressure of the electronic device based on the signal, wherein the sensor assembly further comprises a second force sensor that is physically stacked with the force sensor to transfer forces exerted on the cover glass to each other, the force sensor being capable of detecting forces within a first maximum magnitude and the second force sensor being capable of detecting forces within a second maximum magnitude smaller than the first maximum magnitude.

16. The wearable electronic device as recited in claim 15, wherein the sensor assembly has a ring shape and is positioned on an entire perimeter of the flange.

17. The wearable electronic device as recited in claim 15, wherein the sensor assembly provides mechanical support to the display module.

18. The wearable electronic device as recited in claim 15, wherein the force sensor is physically coupled to the flange and the second force sensor is physically coupled to the display module.

19. The wearable electronic device as recited in claim 15, wherein the second force sensor is capable of causing a transmission, to the processor, of a second signal that is indicative of a touch input applied at the cover glass in response to the second force sensor detecting a force that exceeds a threshold magnitude.

20. The wearable electronic device as recited in claim 15, further comprising:
   a first band feature coupled to the housing; and
   a second band feature coupled to the housing, wherein the first band feature combines with the second band feature to secure the housing with a user.

* * * * *